United States Patent [19]
Hale et al.

[11] Patent Number: 5,255,553
[45] Date of Patent: Oct. 26, 1993

[54] METHOD AND APPARATUS FOR DETERMINING SPECIFIC THERMAL CONDUCTIVITY PARAMETERS OF GASES

[75] Inventors: John M. Hale, Meinier; Eugen Weber, Hinwil, both of Switzerland; Gérard R. Stehle, Machilly, France

[73] Assignee: Orbisphere Laboratories Neuchatel SA, Switzerland

[21] Appl. No.: 840,943

[22] Filed: Feb. 25, 1992

Related U.S. Application Data

[63] Continuation-in-part of Ser. No. 614,133, Nov. 16, 1990, Pat. No. 5,144,831.

[30] Foreign Application Priority Data

Nov. 17, 1989 [CH] Switzerland ................. 4145/89
Feb. 25, 1991 [EP] European Pat. Off. ........ 91810122.1

[51] Int. Cl.$^5$ ............................................. G01N 25/18
[52] U.S. Cl. ............................... 73/19.1; 73/19.12; 73/25.03
[58] Field of Search ................ 73/19.01, 19.05, 19.06, 73/19.1, 19.12, 25.01, 25.03, 31.07

[56] References Cited

U.S. PATENT DOCUMENTS

| | | | |
|---|---|---|---|
| 3,438,241 | 4/1964 | McKinley, Jr. | 73/31.07 |
| 4,201,550 | 6/1980 | Noszticzius | 42/54 X |
| 4,316,382 | 4/1982 | Woodruff | 73/23.2 |
| 4,461,165 | 7/1984 | Kesson | 73/19.1 |
| 4,463,593 | 8/1984 | Parker | 73/19.05 |
| 4,517,135 | 5/1985 | Szerenyi et al. | 73/19.1 |
| 4,550,590 | 11/1985 | Kesson | 73/19.1 |
| 4,563,249 | 10/1986 | Hale | 204/153.1 |
| 5,121,627 | 6/1992 | D'Aoust | 73/19.05 |
| 5,144,831 | 9/1992 | Hale et al. | 73/19.05 |

FOREIGN PATENT DOCUMENTS 0043229 11/1984 European Pat. Off.
0103988 11/1988 European Pat. Off.
0429397 7/1990 European Pat. Off.

OTHER PUBLICATIONS

European Search Report.

Primary Examiner—Hezron E. Williams
Assistant Examiner—Michael Brock
Attorney, Agent, or Firm—Wigman, Cohen, Leitner & Myers

[57] ABSTRACT

A method of determining a specific thermal conductivity parameter of a target gas having a known general thermal conductivity and being contained at a concentration of interest in a fluid medium (F) and comprising: contacting said fluid medium with an organic polymer membrane (11) provided at an interface between said fluid medium (F) and a sensing volume (12) containing a thermal conductivity sensor (13); the membrane (11) is substantially impermeable for any liquid components of the fluid medium (F) but has a known permeability for the target gas; the sensing volume (12) is periodically purged or flushed with a gas having a general thermal conductivity that differs from the thermal conductivity of the target gas; permeation of the target gas through the membrane (11) into the sensing volume (12) is permitted intermittently; at least one time-dependent parameter of the known general thermal conductivity of the target gas that has permeated into the sensing volume (12) is measured; and a parameter of analytical interest, e.g. a partial pressure of the target gas in the fluid (F), is calculated (14, 15) from the time-dependent value obtained and the predetermined permeability of membrane (11) for the target gas.

21 Claims, 7 Drawing Sheets

$$\lambda = x_c \cdot \lambda_c + x_n \cdot \lambda_n \qquad (1)$$

$$\frac{dn_c}{dt} = \frac{V}{RT} \frac{dp_c}{dt} = \frac{D_c S_c A}{b}(P_c - p_c) - \frac{p_c V}{RT} \qquad (5)$$

$$p_t \cdot v/V = (P_c - p_c)/T_c + (P_n + p_c - p_t)/T_n \qquad (9)$$

where: $T_c = b \cdot V/(R \cdot T \cdot A \cdot D_c \cdot S_c)$ and $T_n = b \cdot V/(R \cdot T \cdot A \cdot D_n \cdot S_n)$ $$\frac{dx_c}{d\theta} = x_c^2 + b \cdot x_c + c \qquad (12)$$

where: $\theta = t \cdot \left(\frac{1}{T_c} - \frac{1}{T_n}\right)$ $$c = \frac{P_c/p_t}{1 - T_c/T_n} \quad \text{and} \quad b = -1 - c + \frac{P_n/p_t}{1 - T_n/T_c}$$

*Fig. 12A*

$$\left.\frac{d\lambda}{dt}\right|_{t \to 0} = \frac{(\lambda_c - \lambda_n)}{T_c} \frac{P_c}{P_t} - K_0 \cdot P_c / P_t \qquad (17)$$

$$x_c = \sqrt{c} \cdot \frac{\sinh\left\{\frac{\theta}{2} \cdot (c-1)\right\}}{\sinh\left\{\frac{\theta}{2} \cdot (c-1) + \frac{1}{2} \ln(c)\right\}} \qquad (18b)$$

$$\lambda = 9.258 + 1960 / [10.7464 \cdot V_3 + 83.8178] \qquad (26)$$

Fig. 12B

Legend For Figs. 12A and 12B

| | |
|---|---|
| $P_c$ | = fugacity of component c |
| $\lambda_c, \lambda_n$ | = thermal conductivities of target gas, flushing gas |
| $x_c, x_n$ | = volume fractions of target gas, flushing gas |
| $n_c$ | = number of moles of component c in Volume V |
| $D_c, S_c$ | = diffusion coeffizient and solubility of c in membrane |
| $A, b$ | = area and thickness of membrane |
| $v$ | = flow rate through exit |
| $P_t$ | = atmospheric pressure |

METHOD AND APPARATUS FOR DETERMINING SPECIFIC THERMAL CONDUCTIVITY PARAMETERS OF GASES

CROSS-REFERENCE TO RELATED APPLICATION

This is a continuation-in-part application of pending U.S. patent application, Ser. No. 07/614,133, filed Nov. 16, 1990, now U.S. Pat. No. 5,144,831, in the names of John Martin HALE and Eugen WEBER, said application being based on Swiss application Ser. No. 4145/89-4 filed on Nov. 17, 1989, the priority of which is also claimed in this continuation-in-part application.

BACKGROUND OF THE INVENTION

1. Field of the Invention

The invention generally relates to the art of measuring gaseous substances and, more specifically, to method and apparatus means for determining specific thermal conductivity parameters of a gaseous substance of analytic interest termed "target gas" herein. The term "gaseous" is intended to indicate that the substance of interest is gaseous under normal operating conditions of the subject method, e.g. at temperatures in the range of from $-10°$ to $200°$ C. at pressures ranging from ambient or reduced pressures to 10 bars or more. Typically, the target gas will be contained in a fluid medium; the term "fluid" is used herein to encompass both normally liquid (i.e. liquid under normal ambient conditions) as well as normally gaseous media. Typically, the specific thermal conductivity parameters that are measured according to the invention will not be of primary interest as such but will be used to determine derived parameters of the target gas, e.g. its concentration in a given medium or its pressure.

2. Description of the Prior Art

Numerous methods for monitoring gas concentrations are known and are frequently classified according to the measuring principles involved and/or the characteristic means used for separating the substance of interest from a mixture.

Accordingly, when using a membrane that is permeable for the substance of interest but impermeable to other components of the mixture, the term "membrane-based" analysis is appropriate. When membranes are used mainly because of their separating effect, e.g. between a gas, such as carbon dioxide, and a liquid, such as a carbonated beverage, maximum permeability of the membrane for the gas of interest is generally assumed to be desirable.

For example, a prior art membrane-based method of determining the concentration of carbon dioxide in a beverage, such as beer, as disclosed in EP 0 043 229 and EP 0 103 988, uses membranes that exhibit a maximum permeability for the gas of interest because the actual measuring parameter in these methods is the so-called equilibrium pressure that will build up within a membrane-enclosed chamber in response to the "concentration" (synonymous herein with "partial pressure") of the gas in a liquid that is "external" to the membrane-enclosed space. However, even with membranes made of silicone rubber which are notorious for their high permeability to gases, such as carbon dioxide, relatively long periods of time of typically in the order of 20 minutes may be required until equilibrium of gas pressures.

OBJECTS AND SUMMARY OF THE INVENTION

Hence, a primary object of the present invention is to provide for a novel and improved method of determining various parameters of a target gas by thermal conductivity sensing.

Another important object of the invention is to provide for a novel apparatus that combines specific membrane diffusion and specific thermal conductivity sensing.

Our European patent application No. 90810881 published on May 29, 1991 (Pub. No. 429,397) discloses a method of determining the concentration of gases by pulsatingly measuring specific membrane-related diffusion parameters as a means of determining gas concentrations. The subject matter of said European application being incorporated into our pending U.S. patent application Ser. No. 07/614,133 filed on Nov. 16, 1990, now U.S. Pat. No. 5,144,831. Our pending U.S. application Ser. No. 07/614,133 now U.S. Pat. No. 5,144,831 is incorporated herein in its entirety, especially Example 5 which is presented on pages 18-19 of said pending U.S. application.

We have found upon further research that the combination of membrane diffusion (used as a synonym for permeation herein) with thermal conductivity sensing provides for a novel approach of determining specific parameters of thermal conductivity which, in turn, can be used to determine other gas parameters, such as gas volumes, gas pressures, and gas concentratons, as will be specified in more detail below.

Now, in order to implement these and further objects of the invention that will become apparent as the specification proceeds, the invention provides for a method of determining a specific thermal conductivity parameter of a gaseous (i.e. under the conditions of measurement) constituent or target gas having a known general thermal conductivity and being contained in a fluid medium that may be liquid or gaseous and contains the target gas in an amount ranging from trace amounts to substantial concentrations; if the fluid medium is gaseous it may, and frequently will, contain at least one other gaseous constituent. By the same token, a liquid medium that can be analyzed according to the method of the invention may contain one or more gaseous constituents other than the target gas that have differing general thermal conductivities.

Generally, the inventive method comprises contacting the fluid medium with a membrane preferably made of an organic polymer and provided at an interface between the medium and a sensing space which contains a thermal conductivity sensor of the type known per se and producing an electrical signal as explained in more detail below. The membrane is a relatively thin film, e.g. having a thickness below 300, e.g. from 1.5 to 150, micrometers, typically selected from homopolymeric or copolymeric fluoro(hydro)carbons and is substantially impermeable for any liquid components of the fluid medium but has a known or previously determined permeability for the target gas. The sensing space is periodically filled, i.e. to the extent of displacing any gas or gas mixture previously contained in the sensing space, with a flushing or purging gas having a known general thermal conductivity that differs measurably (i.e. under the conditions of the present method) from the known general thermal conductivity of the target gas and, preferably, is substantially non-reactive with any parts of the apparatus used to carry out the novel method.

Intermittently, i.e. between any two subsequent filling steps, the target gas is permitted to permeate through the membrane and into the sensing space, e.g. during a permeation phase of typically in the range of from about 20 to about 60 seconds. Longer as well as shorter periods of permeation of the target gas from the fluid medium through the membrane into the sensing space could be used if practical. Then at least one time-dependent parameter of the general thermal conductivity of the target gas that has permeated into the sensing space is measured by means of the thermal conductivity sensor provided in the sensing space; finally, the target gas parameter of analytical interest, e.g. the concentration of the target gas in the fluid medium or its pressure, is calculated from the at least one time-dependent value just measured and from the predetermined permeability of the membrane for the target gas, preferably by means of a digital computer.

The readings obtained can be indicated on an analog or digital display so as to represent the desired analytical parameter of the target gas, e.g. its concentration or partial pressure in the fluid medium that contacts the membrane.

The sensing space can be in continuous and direct communication with an ambient space, e.g. via an open channel or conduit provided that diffusion of ambient gas into the sensing space is prevented.

According to a second important embodiment the invention comprises an apparatus for carrying out the novel method, i.e. for determining a specific thermal conductivity parameter of a target gas having a known general thermal conductivity and being contained in a fluid medium. The apparatus according to the invention comprises a sensing space, e.g. constructed in the manner of a diffusion cell and containing a thermal conductivity sensor of the type known per se and capable of producing an electrical output signal; a membrane of the type and thickness exemplified above is provided as an interface between the fluid medium and the sensing space and prevents significant permeation of any liquid components of the fluid medium; the permeability of the membrane for the target gas is known or determined by way of calibration prior to actual operation of the apparatus, e.g. by exposing the outer membrane surface to a calibrating fluid that contains the target gas at a known concentration. The apparatus has an inlet and an outlet for the flushing gas specified above. Preferably, a substantial portion of the sensing space is filled with an inert material of substantial mechanical strength so as to reduce the volume of the sensing space while presenting a support for the membrane which counteracts any pressure that may act upon the membrane during operation of the apparatus. The inlet for the flushing gas opens into one end of the support body while the outlet for the flushing gas commences at an opposite end of the support so that the gas will flush substantially the entire inner volume of the sensing space.

A valve, e.g. of the solenoid-operated type, is preferably arranged in the inlet conduit for the flushing gas and is actuated automatically after a predetermined period of time thus terminating the preceding permeation period and returning the apparatus to "zero"-conditions as regards the target gas. In other words, the beginning and end of any flushing period terminates the preceding permeation period and starts the subsequent permeation period.

Preferably, the apparatus according to the present invention further includes means to transform the normally analog signal produced by the thermal conductivity sensor into a digital signal which, in turn, is fed into the computer which receives the membrane permeation parameter as a further input as well as a timing signal.

BRIEF DESCRIPTION OF THE DRAWINGS

The invention will be better understood and objects other then those set forth above will become apparent when consideration is given to the following detailed explanation thereof. Such explanation, makes reference to the annexed drawings in which:

FIG. 12A and 12B are a sequence of equations for calculating analytical parameters of interest.

DETAILED DESCRIPTION OF THE PREFERRED EMBODIMENTS

Describing the drawings it is to be understood that only those details are explained as are needed for one skilled in the art to understand the principles and concepts of the present invention.

Figure 1:
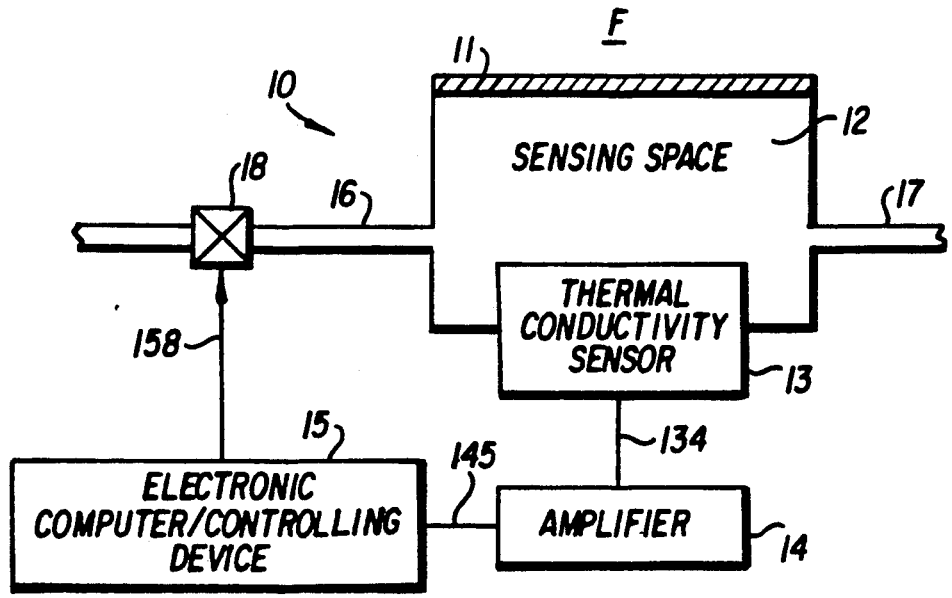
FIG. 1 is a block diagram illustrating the essential elements of the inventive method.

Turning to FIG. 1, the block diagram or system 10 shows a preferred general embodiment of the invention. Sensing space 12 containing a thermal conductivity sensor 13 is separated from a fluid F by a membrane 11 which is permeable for the target gas but is substantially impermeable for any liquid components of the external fluid F. Fluid F can be regarded as the external phase of system 10 and corresponds with the "fluid medium" set forth above. Sensing space 12 also serves as a receiving space and as a flushing volume.

While specific examples of suitable membranes will be given below, polymer films of the type known in the practice of membrane-enclosed analytical devices can be used for the invention. As briefly mentioned above (co)polymeric halo(hydro)carbons are suitable, i.e. carbon-based organic polymers in which at least some hydrogen atoms are replaced by halogen, preferably fluorine, and which have a film-forming moleculuar weight. Teflon polymers represent a typical example.

As also briefly mentioned before, it is an essential feature of the invention that the rate of permeation of the target gas through membrane 11 must be known when carrying out the calculation step of the method according to the invention. This is in contrast with most prior art analytical methods using semi-permeable membranes of the type separating a permeating gas from a non-permeating liquid because the normal conventional approach is to use membranes having a high permeability for the target substance and substantially no permeability for any non-target substance, whereas the exact specific permeability of the membrane actually used is of secondary interest, if at all. Obviously, such permeability or permeation of the target gas through a specific type (involving chemical structure, molecular orientation and physical structure) of membrane will depend upon membrane geometry and pressure gradient across the membrane; however, the data for calculation in accordance with the inventive method can be provided by the source of the membrane material or that of the apparatus disclosed herein, or be established in a calibration step prior to commencing a determination according to the invention. Preferably, such calibration is made with the apparatus actually employed for the present method using an external fluid F containing the target gas at a known pressure or concentration and at a known temperature.

Preferably, a membrane for use in the invention should have an intermediate permeability in the sense that permeation of the target gas occurs rapidly enough for a quick response yet substantially preventing or minimizing depletion of the target gas in the external fluid adjacent the membrane interface. Also, the membrane preferably should have a low time constant for diffusion of the target gas therethrough because calculation of the parameter of interest is simplified if it can be assumed that diffusion occurs in "steady state", i.e. that the pressure gradient of the target gas within the membrane is an essentially linear function of position.

In practice, membranes having a thickness in the range of from 3 to 125 micrometers made from polytetrafluoro ethylene (PTFE), polymeric fluorinated ethylene-propylene (FEP), copolymers of ethylene and tetrafluoro ethylene (ETFE) or similar polymers have been found to be suitable and are cited by way of non-limiting examples.

Preferably, membrane 11 will be supported mechanically to withstand expected pressures of the external fluid F in a given application of the invention but this is not shown in FIG. 1 and will be explained later. However, neither lower nor upper limits of the pressure of external fluid F are expected to be critical, and typical applications of the inventive method may involve external pressures in the range of up to 100 bars or more.

Preferably, the volume of the sensing or receiving space 12 is as small as apparatus design permits, e.g. in the range of from about 0.01 to about 1 milliliter; it is to be noted that even smaller volumes would be advantageous for the method of the invention but may not be compatible with simple design and ease of operation of the apparatus for use in carrying out the novel method.

Suitable devices for use as thermal conductivity sensors 13 according to the invention are available commercially in various forms. Typical and preferred examples of suitable sensors 13 are those of the semi-conductor type sold by the Hartmann & Braun Division of Mannesmann, Frankuft/Main, Germany. Details of design and operation of such sensors are disclosed in publicly available sales information literature and do not require detailed discussion herein. Preferably, sensor 13 also includes a thermistor for measuring the ambient temperature to permit compensation of the raw thermal conductivity signal obtained.

An inlet conduit 16 of system 10 serves to introduce a purging or flushing gas from a pressurized source (not shown) when valve 18 is opened by a signal, e.g. generated by and received from an electronic computing-/controlling device 15 via an operative connection 158. Such operative connection can be made by conventional electric, electronic, hydraulic, pneumatic or mechanical means.

The purpose of flushing volume 12 is to drive out therefrom any other gases that have diffused into volume 12 via membrane 11. Flushing should be sufficient to return system 10 to "zero-condition", i.e. until volume 12 is completely filled with flushing gas before a subsequent permeation and measuring cycle is initiated by closing valve 18. Such "zero-condition" may, but need not, involve a zero reading of the specific parameter that is being measured with the apparatus. A minor portion of the flushing gas may permeate through membrane 11 into fluid F but the major part of the flushing gas stream (containing an increasing portion of the flushing gas as long as there is a purging effect) exits from volume 12 through outlet conduit 17.

While a valve might be used to close conduit 17, it is preferred according to the invention that conduit 17 is not mechanically closed but that it will maintain space 12 in continuous fluid communication with the ambient while preventing back-diffusion therefrom. To this end, conduit 17 may have a sufficient length and/or constricting internal diameter; these dimensions will depend upon various parameters of operation including length of the flushing period and gas pressure so that no generally applicable limits can be given but can be established for any given situation by means of a few and simple tests. As an illustrative example, conduit 17 might be a tube having a length of, say, 300 mm and an internal diameter of 1 mm; typically, a length: diameter ratio of a tubular outlet of at least 100:1 will be suitable for many purposes.

Upon operation of system 10 according to the invention and assuming that volume 12 is completely filled with the flushing gas, closure of valve 18 permits that target gas (by definition differing from the flushing gas as regards thermal conductivity) will permeate through membrane 11 at a certain rate or flux determined by the specific and known permeability of membrane 11. Any partial pressure of the target gas greater than zero will be able to cause controlled significant permeation of the target gas contained in fluid F through membrane 11 into volume 12 and, hence, to change the specific thermal conductivity of the gas contained in volume 12. Thus, an electrical signal commensurate with permeation of target gas will be generated by sensor 13 and can be fed, with or without digital/analog conversion, via an electrical connection 134 into an amplifier 14 which, in turn, feeds the signal thus produced into a microprocessor provided in the computing/controlling device 15.

Figure 2:
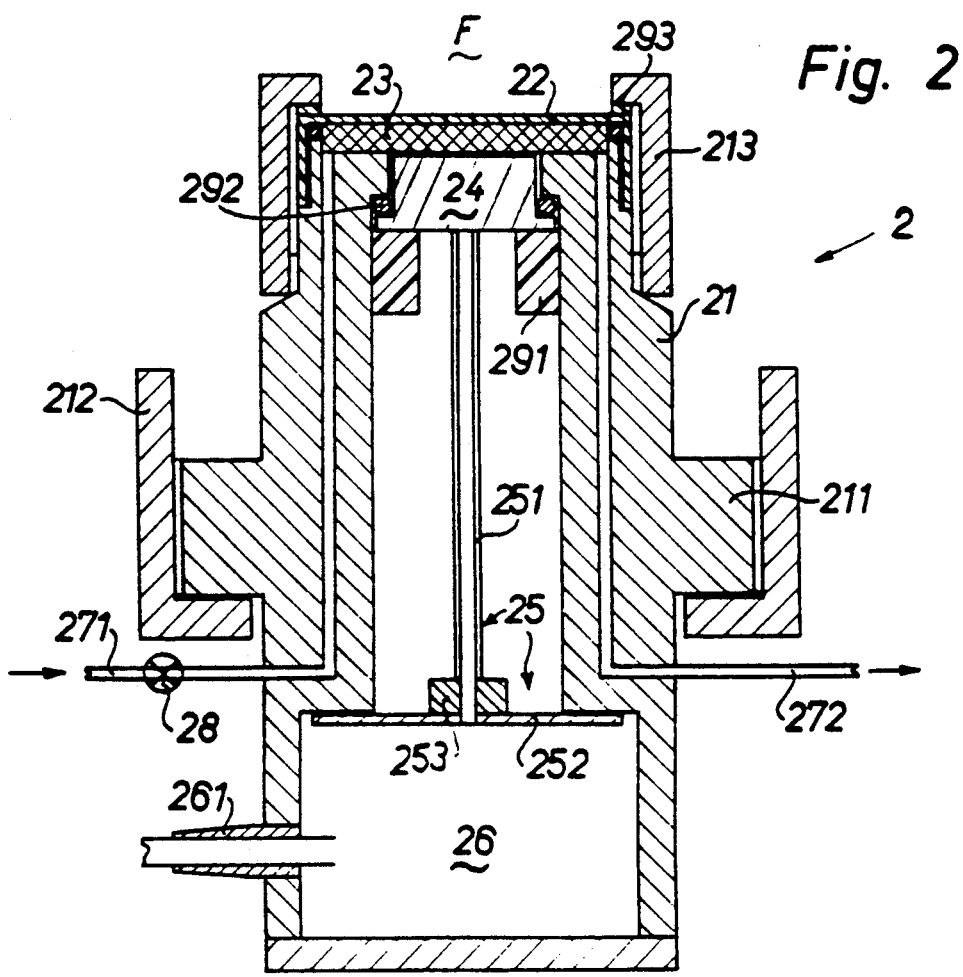
FIG. 2 is a diagrammatic sectional view of an apparatus suitable for carrying out the inventive method and incorporating preferred apparatus features according to the invention.

FIG. 2 is a diagrammatic sectional view of an apparatus or probe 2 according to the invention comprising a generally tubular body 21 having a shoulder 211 for connection with a flange 212 or other mounting device of a conduit, tank or the like (not shown) that contains or conducts the fluid medium which is to be analysed by the inventive method.

A sealing cap 213 is screwed onto or otherwise connected with body 21 so as to sealingly hold a polymer membrane 22 on a membrane support 23, e.g. made of perforated metal, a mineral glass, ceramic or cermet so as to effectively support membrane 22 against elevated pressures due to continuous operating conditions or to accidental overpressures while, at the same time, providing a sensing space that is small enough to permit an easily measurable change of the target gas parameter of interest yet permitting rapid gas diffusion. The terms "perforated" or "porous" as used herein are intended to refer to a generally solid structure having a multiplicity of openings, voids or "pores" to permit gas diffusion and passage. The volume defined by substantially all openings or voids of support 23 is termed the "internal" volume of support 23.

Sealing and membrane holding means are provided to assure that any passage of gas from the external fluid F into support 23 is by way of permeation through membrane 22. A commercial thermal conductivity sensor 24 (e.g. type TCS 208) is held close to, or preferably in pressure contact with, support 23. It is to be noted that the "internal" volume of support 23 does, in essence, define the entire volume of the sensing space 12 shown in FIG. 1. In other words, sensor 24 need not, and preferably does not, provide substantial additional volume to the sensing space which, in the illustration of FIG. 2, is essentially defined by the internal volume of support 23. Preferably, sensor 24 additionally includes a thermistor capable of sensing ambient temperatures for compensation purposes.

Sealing means, e.g. an annular seal 293 and an O-ring 292, are provided to prevent by-passing gas diffusion into the interior of body 21. A support ring 291 made of a polymer as indicated in FIG. 2 or of another material is connected with body 21, e.g. by a thread (not shown). Alternatively, the support ring may be omitted or formed as an integral part of body 21. A connector means 25 is provided to receive a conduit (not shown) for passing signals from sensor 24 to a compartment 26 that encompasses conventional analog electronics (not shown) including or not conventional amplifier means (not shown). A cable port 261 is provided for output/input connection of the electronics in compartment 26 with a coordinated computing/controlling device (not shown in FIG. 2) of the type explained above.

In the preferred apparatus embodiment shown in FIG. 2 the connector means 25 include an elongated tube 251, a base plate 252 and an annular connector 253, all of which may cooperate to hold sensor 24 in pressure contact with membrane support 23 and/or to protect the electronics within compartment 26 from detrimental conditions at the membrane end of probe 2. Such structure of probe 2 is particularly useful when used to determine gas parameters in an environment that is exposed to elevated temperatures, e.g. in the range of from about 100° to 200° C. or more depending upon permissible conditions of environment or operation of sensor 24. Intrinsic operability at such elevated temperatures is an added advantage of the invention because many important industrial applications require sterilisation treatment, e.g. with hot steam, or operation at elevated temperatures. The materials for the components of probe 2 will be selected in view of the intended operation conditions. For example, body 21 and the sealing ring 213 are made of stainless steel, titanium or teflon (polymers or copolymers of tetrafluoro ethylene).

A feeding conduit 271 or a fitting for connection with such conduit is provided to pass a flushing gas from a source (not shown) via a valve 28, capable of being operated by remote and automated control, and through body 21 as well as the inner volume of support 23 to an outlet conduit 272 in a manner explained above in connection with FIG. 1. Generally, valve 28 should be as close as possible to the receiving space, i.e. the inner volume of support 23, and the free inner volume of conduit 271 between valve 28 and support 23 should be kept to a minimum if the response of probe 2 to changes of the properties of the target gas is to have optimum performance with regard to sensitivity, short response times and reproducibility.

The flushing or purging gas should generally be selected in view of a number of factors: firstly, it should have a thermal conductivity value that is different from that of the target gas; such values are well known for all pure gases and are in the general range of from about 3 to 200 milliwatt per meter per degree Kelvin (mW/mK) when measured between zero and 100° C. Typically, Freon 11 ($CClF_3$) is at the lower end while helium and hydrogen are at the higher end; carbon dioxide has an intermediate thermal conductivity.

Secondly, the flushing gas should be substantially inert under the conditions of measurement and be essentially non-reactive with the components of the apparatus and with the target gas. On the other hand, if the target gas is contained as a minor constituent in a normally inert fluid medium, the restriction of inertness does not apply, or to a lesser degree. Further, pure flushing gases are preferred over mixtures since this helps to keep calculation simple. Further, if the target gas is contained as a minor constituent or impurity in a fluid medium consisting essentially of another or "principle" gas, it is preferred to use this principle gas (or another gas with the same or similar thermal conductivity) as the flushing gas because this facilitates evaluation of the response by substantially "blanking out" the influence of the principle gas on the specific thermal conductivity parameter that is actually measured when practicing the invention.

The length of the purging periods, i.e. the time between opening of valve 28 and the subsequent closing, should be long enough to provide for complete purging of the sensing space without interfering with the sensing operation. In practice, complete purging can be obtained in a probe 2 substantially as disclosed herein with flushing periods of about 1 to about 10 seconds. Flushing periods of about 5 seconds have been found to be operative for many purposes of the invention.

Flushing of the sensing space is effected periodically, i.e. in a sequence of flushing periods of equal length with intermittent periods, also termed "measuring periods" herein where the influx of flushing gas and permeation of the target gas into the sensing space is permitted. The diffusion rate of flushing gas through the direct communication does not exceed the rate of diffusion of the flushing gas from the sensing space through the membrane into the fluid medium.

Now, since the method of the invention is based upon the time dependence of the specific thermal conductivity of the mixture of flushing gas and target gas in the sensing space during each measuring period, such periods will be of equal length and should be long enough for collecting and evaluating an adequate quantity of data for accurate analysis. On the other hand, the measuring periods should be so short that the concentration of the target gas in the external fluid does not change substantially during one measuring period. Depending upon the specific application, measuring periods of a few seconds up to a few minutes are considered typical for practice of the inventive method. When determining, for example, the nitrogen content of carbon dioxide or vice-versa, typical measuring periods are in the range of from about 20 to about 60 seconds.

In other words, when operating the inventive method for any length of time, or continuously, a virtually endless sequence of flushing periods, e.g. of 5 seconds duration, and intermittent measuring periods, e.g. of 60 seconds each, will be effected while the inventive method is practiced, e.g. when continuously monitoring the partial pressure of the target gas in a gaseous or liquid external medium.

The inventive method can be used, inter alia, to actually control the composition of a fluid medium by monitoring the partial pressure of a target gas in a fluid medium and using the results of the inventive method as input parameter of a device for feeding or removing target gas; the device is activated when the partial pressure of the target gas of interest deviates from a predetermined desired value. Devices of this type are known per se for various gases of interest and/or can be made by those skilled in the art.

Figure 3:
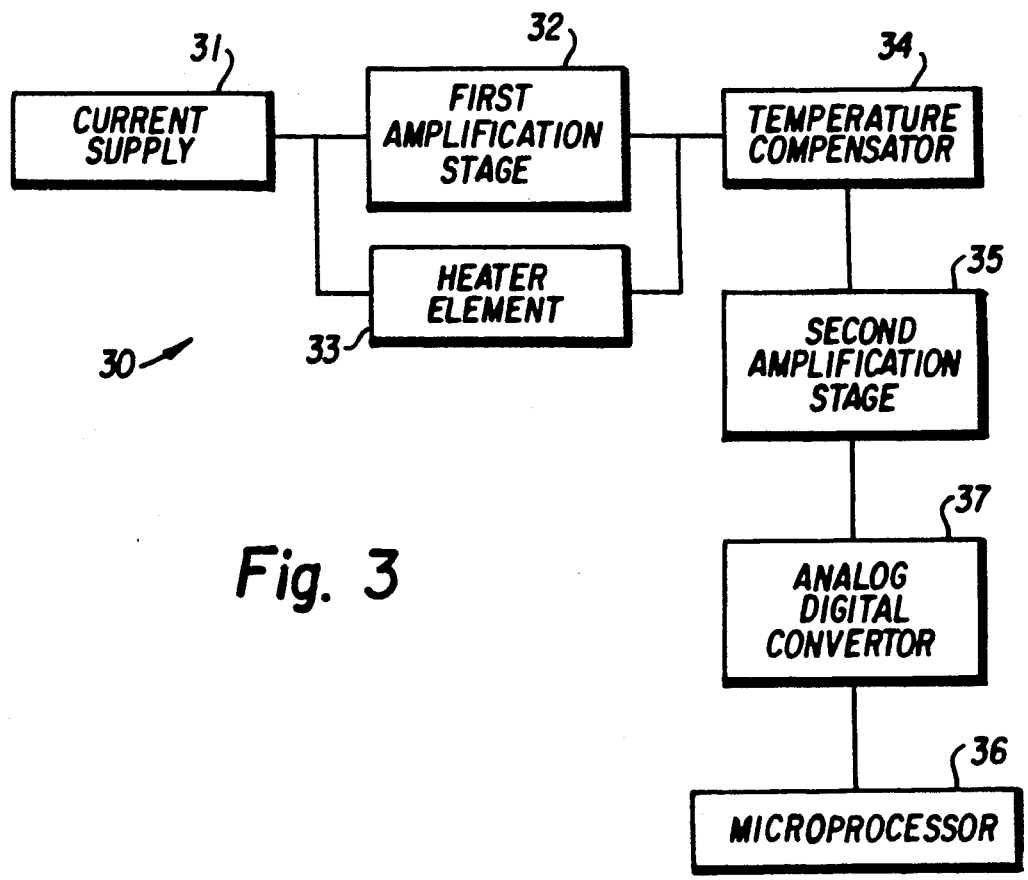
FIG. 3 is another block diagram illustrating an example of thermal conductivity sensing.

FIG. 3 is intended to illustrate requirements of the electronic circuit 30 for use in the invention. Current supply 31 is connected with heater element 33 of a thermal conductivity sensor and with a parallel first amplifier or first amplification stage 32; the combined outputs of 32 and 33 are fed first into the temperature compensator 34 of the thermal conductivity sensor and then into a second amplifier 35. The resulting analog signal is fed into an analog/digital converter 37 and into microprocessor 36 for conversion into an output signal display (not shown). The specifics of such circuit depend upon the thermal conductivity sensor and upon the input facilities of the microprocessor in a manner obvious to those skilled in the art.

In a practical realisation of the invention the heater resistance 33 of the thermal conductivity sensor required a heater current in the order of 6 mA generated by current supply 31; the steady state resistance reached by this specific embodiment represented the raw measure of the specific thermal conductivity and was converted into voltage in the first amplification stage 32. This voltage was sensitive to the temperature of the ambient so that temperature compensation 34 was needed in the second amplification stage 35. The resulting signal, preferably amplified in a third amplification stage (not represented in FIG. 3), was fed into the A/D converter 37 and the resulting digital output was processed by microprocessor 36. As a matter of practice, all analog elements of the circuit up to and including the final amplifier can be made from surface mounting devices applied to a miniature printed circuit board and incorporated in probe 2 as illustrated in FIG. 2 above. In this way, only high level signals are passed so as to minimize electromagnetic interference.

The microprocessor 15 (FIG. 1) or 36 (FIG. 3) should be capable of receiving signals from the thermal conductivity sensor, the optional ambient temperature sensor provided therein, and from a further optional temperature sensor provided in the external fluid medium if temperature compensation of the permeability of the membrane is to be achieved. Preferably, the microprocessor 36 should further be capable to actuate valve 28. If the invention is applied for controlling the partial pressure of the target gas in a medium, microprocessor 36 should also control the device that adds or removes target gas from the monitored medium.

The algorithm required for the calculation step of the inventive method can be set up on the basis of the assumption that the sensing space contains a volume in which the gas is homogeneous when measured. In the course of the substantially endless succession of flushing periods and measuring periods as explained above, the flushing gas is assumed to have a known general thermal conductivity; further, it is assumed that measurement is effected at ambient atmospheric pressure. Considering the specific thermal conductivity of the mixture of flushing gas and target gas within the sensing space, the mass balance therein as well as the flow rate of gas at the exit of the sensing space and the time dependence of the specific thermal conductivity, the initial slope of the curve representing the specific thermal conductivity of the mixture of flushing gas and target gas in the sensing volume can be calculated and a sequence of calculations is represented in FIGS. 12A and 12B.

EXAMPLES

The invention will be further illustrated without limitation by means of the following examples in which percents and parts are by weight and degrees are in centigrade unless otherwise noted. "K" stands for "degree Kelvin"; "mils" are units of 25.4 micrometers as used by most commercial suppliers.

EXAMPLE 1

Determination of Carbon Dioxide in the Presence of Nitrogen

Figure 7:
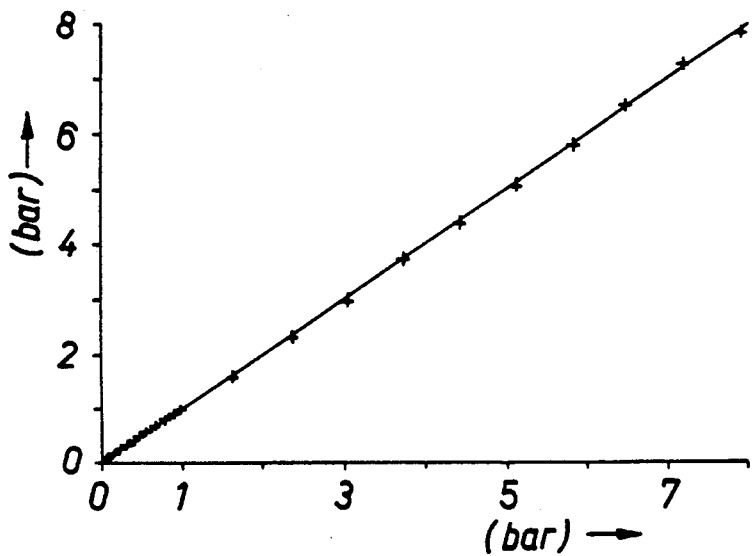
FIG. 7 is a diagram illustrating determination of the concentration of carbon dioxide in a fluid medium consisting of gaseous nitrogen and gaseous carbon dioxide.

Mixtures of carbon dioxide in the presence of nitrogen with various partial pressures of carbon dioxide were prepared for testing over two orders of magnitude. Partial pressures greater than atmospheric pressure were made by pressurizing pure carbon dioxide and those below atmospheric pressure were obtained with a conventional gas mixing apparatus. The resulting gas mixture of known composition was passed over membrane 22 of a probe 2 substantially as shown in FIG. 2. The membrane had a thickness of 1 mil and consisted of commercial perfluoroalkoxy polymer (PFA); measurement was made at an atmospheric pressure of 0.975 bar and at 25°. Pure nitrogen was used as flushing gas so that the measuring system was insensitive to this gas. Calibration was effected in pure carbon dioxide. The calibration constant $K_0$ (cf. equ. 17) at 25° was $8.93 \cdot 10^{-3}$ (W/m·K·s). FIG. 7 is a graphic presentation of the results obtained showing the indicated partial pressure of carbon dioxide in bar on the ordinate versus the true partial pressure of carbon dioxide, again in bar, on the abscissa.

EXAMPLE 2

Influence of Permeability of the Membrane on the Calibration Constant

Various values of the calibration constant $K_0$ (equ. 17) were measured for a series of different membranes using hydrogen gas as the target gas and nitrogen as the flushing gas according to the inventive method using an apparatus substantially as shown in FIG. 2. The same quantities were determined by a prior art method of a different type, i.e. by amperometric analysis as disclosed in U.S. Pat. No. 4,563,249.

Figure 4:
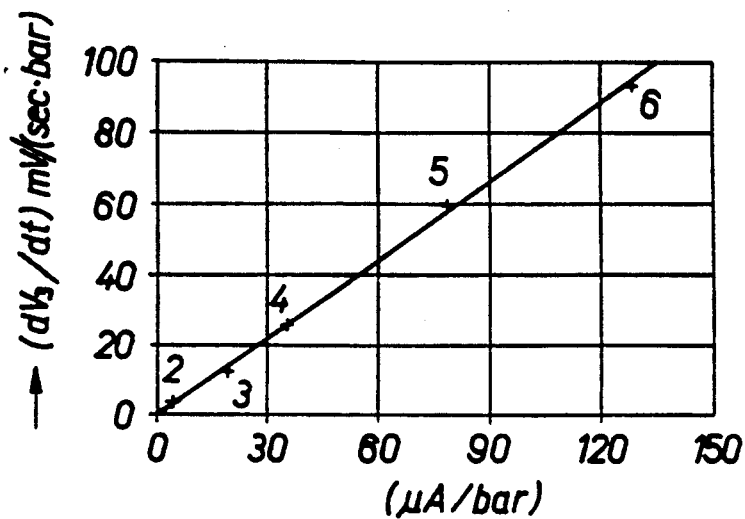
FIG. 4 is a diagram showing the influence of membrane permeabilities upon thermal conductivity sensing.

The results are illustrated in FIG. 4 where the values obtained by thermal conductivity determination are given on the ordinate in mV per second per bar while the current sensitivity obtained by the amperometric method are represented on the abscissa in microamperes per bar. The linearity of the curve obtained is excellent and establishes that the membrane does control the rate of change of the specific thermal conductivity of the target gas in the sensing space. The points of measurement in the diagram of FIG. 4 are for membrane materials and thicknesses as follows:

2 = polyvinyl fluoride (PVF); 0.5 mil.
3 = copolymer of ethylene and monochloro trifluoro ethylene (E-CTFE); 1 mil.
4 = copolymer of ethylene and trifluoro ethylene (ETFE); 1 mil.
5 = ETFE; 0.5 mil.
6 = perfluoro alkoxy polymer (PFA); 1 mil.

EXAMPLE 3

Wide Range Study

Figure 5:
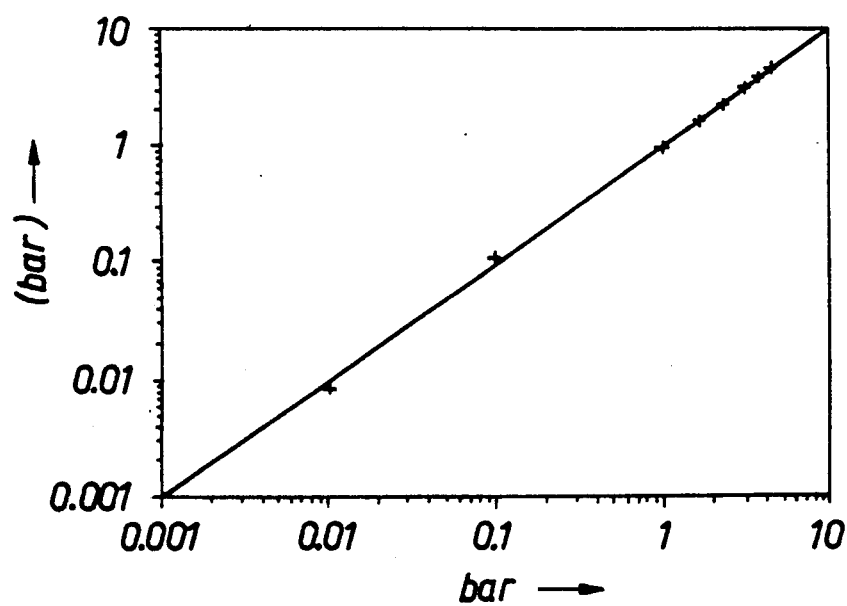
FIG. 5 is a diagram illustrating determination of hydrogen as target gas in nitrogen as flushing gas.

With an apparatus substantially as shown in FIG. 2 using a PFA membrane, gaseous mixtures of hydrogen as target gas and nitrogen as flushing gas with known values of the partial pressure of the target gas were compared with those determined according to the invention over three decades of magnitude. The results are shown in FIG. 5 where the true partial pressures of hydrogen (in bar) are plotted on the abscissa against the indicated values obtained according to the invention (again in bar) on the ordinate. The lower limit of detectability of hydrogen in nitrogen was about 0.1% by volume at which level the error amounted to plus/minus 5%. Both the accessible range of concentration of the target gas well as the detectability limit can be shifted almost at will by using different membranes.

EXAMPLE 4

Calculation of Specific Thermal Conductivity Versus Time

Figure 6:
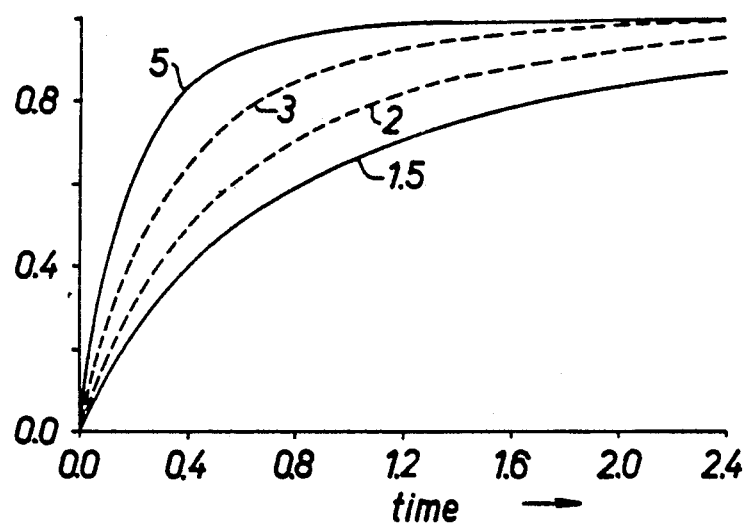
FIG. 6 is a diagram showing thermal conductivity versus time.

FIG. 6 illustrates the time variation of the fraction of the target gas for several values of the parameter c (calculated according to equ. 18b). Since the value of c can be derived from the slope at short times, the time constant (for the accumulation of the flushing gas) for permeation of the flushing gas could be fitted from equ. 18b.

EXAMPLE 5

Determination of Nitrogen in Carbon Dioxide

Figure 8:
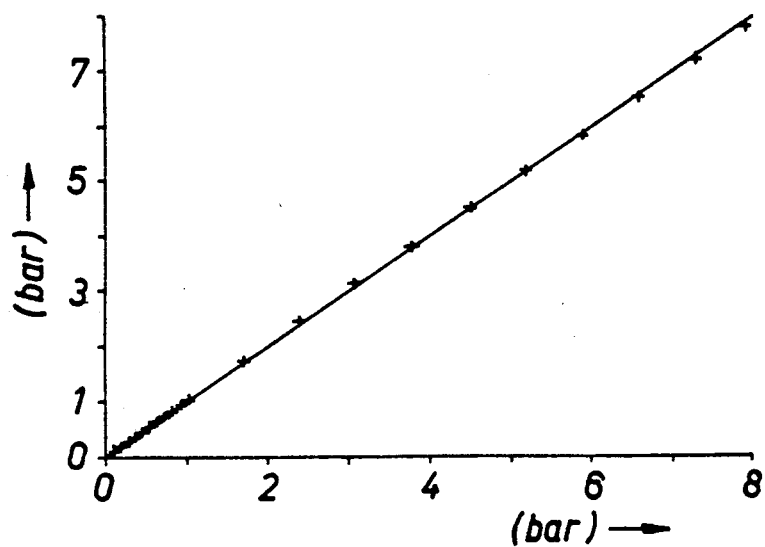
FIG. 8 is a similar diagram showing determination of nitrogen in a fluid consisting of a gaseous mixture of carbon dioxide and nitrogen.

The procedure of Example 1 was followed but reversing the function of the gases, i.e. with nitrogen as the target gas and carbon dioxide as the flushing or purging gas. The results obtained are shown in FIG. 8 as crosses for the points actually measured. Again, excellent linearity was observed.

EXAMPLE 6

Calculation of Thermal Conductivity from Voltage

Because determination in line with equ. 26 introduces a number of parameters dependent upon the apparatus used, a more convenient method for practical purposes is based upon a generalisation of equ. 26. To this end, amplifier voltages are measured and compared with known thermal conductivites for a series of different gases.

Figure 9:
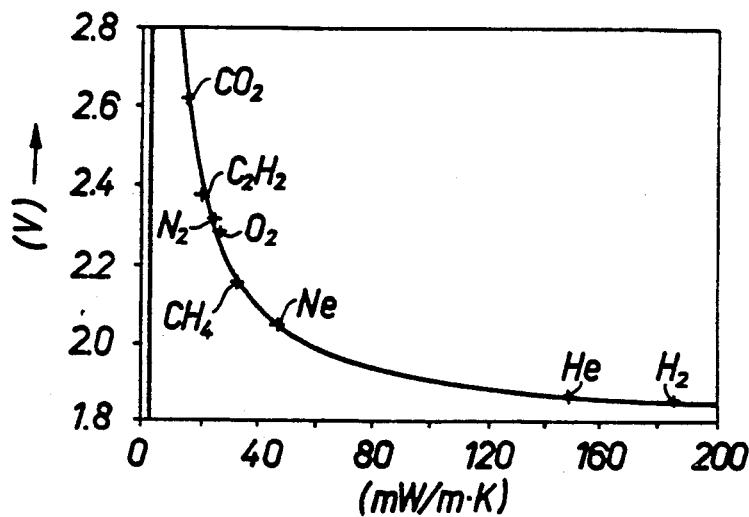
FIG. 9 is a diagram showing the relation of amplifier voltage versus thermal conductivity for various gases at 25° C.

Generalisation of equ. 26 yields:

$$\lambda = c_1 + c_2/[V_2 - c_3] \qquad \text{(equ 26a)}$$

and when solving this for the constants from the data for carbon dioxide, neon and hydrogen it was found that $c_1 = 2.3635$, $C_2 = 11.452$ and $c_3 = 1.7937$. The data obtained are shown in FIG. 9 where the voltage output is given on the ordinate and thermal conductivity on the abscissa.

Figure 10:
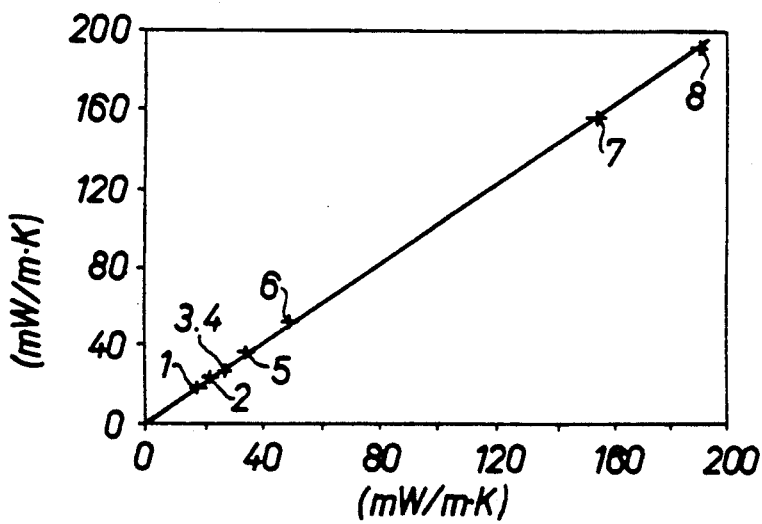
FIG. 10 is another diagram showing the relation between calculated and measured values of thermal conductivity.

FIG. 10 shows a comparison of the thermal conductivites (in mW per m per K) calculated according to the invention with equ. 26a and shown on the ordinate with known thermal conductivities in the same units as those shown on the abscissa. Eight values numbered 1–8 are represented indicating a satisfactory degree of linearity and confirming the validity of equ. 26a.

EXAMPLE 7

Flushing Gas Influence

Figure 11:
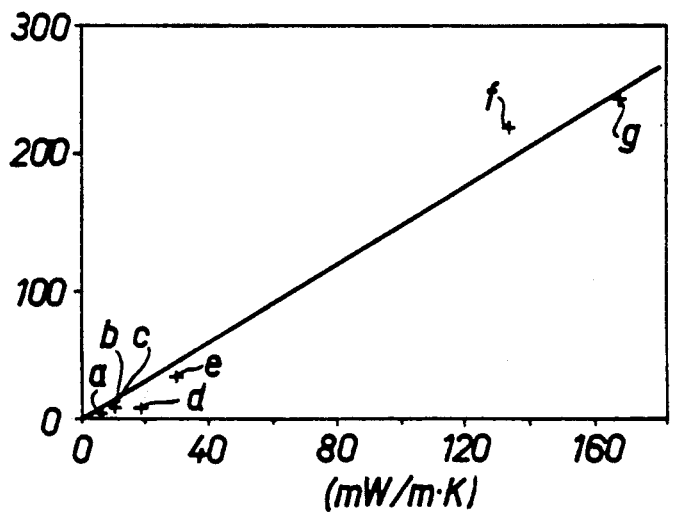
FIG. 11 is a diagram showing carbon dioxide measurements with various flushing gases.

A probe substantially as shown in FIG. 2 was exposed to carbon dioxide as target gas at 1 bar and 25°. Different flushing gases were used to purge the sensing space. In each case the calibration constant $K_0$ was measured and is indicated in the diagram of FIG. 11 on the ordinate with the thermal conductivity difference indicated on the abscissa. It is apparent from this graph that the sensitivity of the inventive method is enhanced if the flushing gas used has a thermal conductivity that differs substantially from that of the target gas. The symbols in FIG. 11 are as follows: a = carbon dioxide, b = nitrogen, c = oxygen, d = methane, e = neon, f = helium, g = hydrogen.

It is assumed that virtually any gas can be used as target gas, and that most gases can be used as flushing gas excluding but those which are extremely aggressive and/or toxic, such as the halogens, hydrohalogens, etc. Generally, inert gases including nitrogen, carbon dioxide, rare gases, gaseous hydrocarbons or halohydrocarbons are preferred as flushing gases keeping in mind the need to maintain a suitable difference of thermal conductivity between target gas and flushing gas.

Suitable modifications of the preferred embodiments discussed above can be made without departing from the inventive concepts disclosed herein and will be apparent to those experienced in the art. So, while certain embodiments of the invention have been explained in some detail, it is to be understood that the invention is not limited thereto but may be otherwise embodied and practiced within the scope of the following claims.

We claim:

1. A method of determining a specific thermal conductivity parameter of a gaseous constituent of interest having a known general thermal conductivity and being contained at a concentration of interest in a fluid medium, comprising the steps of:

(A) contacting said fluid medium with a membrane provided at an interface between said fluid medium and a sensing space containing a thermal conductivity sensor; said membrane being substantially impermeable for any liquid components of said fluid medium but having a known permeability for said gaseous constituent;

(B) filling said sensing space with a flushing gas having a general thermal conductivity which differs from said general thermal conductivity of said gaseous constituent;

(C) permitting permeation of said gaseous constituent through said membrane into said sensing space;

(D) measuring at least one time-dependent parameter of said known general thermal conductivity of said gaseous constituent that has permeated into said sensing space;

(E) calculating said concentration of said gaseous constituent of interest from said at least one time-dependent value obtained in step (D) and said known permeability of said membrane for said gaseous constituent; and (E) repeating steps A–E for a desired number of repetitions so as to periodically fill said sensing space with a flushing gas and to intermittently permit permeation of said gaseous constituent.

2. The method of claim 1 wherein said sensing space is in communication through a conduit with an ambient space so as to permit flow of said flushing gas and wherein diffusion of said flushing gas through said conduit is limited to a diffusion rate that does not exceed diffusion of said flushing gas from said sensing space through said membrane into said fluid medium.

3. The method of claims 1 or 2 wherein an analog signal obtained in said measurement of step (D) is converted into a digital signal; and wherein said digital signal is used in step (E) for calculating said concentration by means of a digital computer.

4. The method of claim 3, wherein said membrane comprises a film of an organic fluorocarbon polymer having a thickness in the range of from 1.5 to 150 micrometers.

5. The method of claim 3, wherein said flushing gas is selected from substances that are substantially non-reactive when used under operating conditions of the method.

6. The method of claim 3 wherein said permeation of said gaseous constituent through said membrane in step (C) is permitted during a period of from 20 to 60 seconds.

7. The method of claims 1 or 2, wherein said membrane comprises a film of an organic fluorocarbon polymer having a thickness in the range of from 1.5 to 150 micrometers.

8. The method of claim 7, wherein said flushing gas is selected from substances that are substantially non-reactive when used under operating conditions of the method.

9. The method of claim 7, wherein said permeation of said gaseous constituent through said membrane in step (C) is permitted during a period of from 20 to 60 seconds.

10. The method of claims 1 or 2, wherein said flushing gas is selected from substances that are substantially non-reactive when used under operating conditions of the method.

11. The method of claim 10, wherein said permeation of said gaseous constituent through said membrane in step (C) is permitted during a period of from 20 to 60 seconds.

12. The method of claims 1 or 2, wherein said permeation of said gaseous constituent through said membrane in step (C) is permitted during a period of from 20 to 60 seconds.

13. An apparatus for determining a specific thermal conductivity parameter of a gaseous constituent having a known general thermal conductivity and being contained at a concentration of interest in a fluid medium comprising:

(A) a sensing space containing a thermal conductivity sensor, said sensor measuring a thermal conductivity value;

(B) a membrane provided as an interface between said fluid medium and said sensing space; said membrane being substantially impermeable for any liquid components of said fluid medium but having a known permeability for said gaseous constituent;

(C) means for periodically filling said sensing space with a flushing gas having a general thermal conductivity which differs from said general thermal conductivity of said gaseous constituent;

(D) timing means for measuring periods of permeation of said gaseous constituent through said membrane into said sensing space between successive fillings of said sensing space with said flushing gas; and (E) means for calculating a rate of change of thermal conductivity of the gas in said sensing space from said thermal conductivity value together with said periods of permeation, and for calculating said concentration of said gaseous constituent of analytical interest from said rate of change of thermal conductivity and said predetermined permeability of said membrane for said gaseous constituent.

14. A method of controlling the concentration of a target gas in a fluid medium comprising determining actual concentration of said target gas in said medium by determining a specific thermal conductivity parameter of a gaseous constituent of interest having a known general thermal conductivity and being contained at a concentration of interest in a fluid medium, comprising the steps of:

(A) contacting said fluid medium with a membrane provided at an interface between said fluid medium and a sensing space containing a thermal conductivity sensor; said membrane being substantially impermeable for any liquid components of said fluid medium but having a known permeability for said gaseous constituent;

(B) filling said sensing space with a flushing gas having a general thermal conductivity which differs from said general thermal conductivity of said gaseous constituent;

(C) permitting permeation of said gaseous constituent through said membrane into said sensing space;

(D) measuring at least one time-dependent parameter of said known general thermal conductivity of said gaseous constituent that has permeated into said sensing space;

(E) calculating said concentration of said gaseous constituent of interest from said at least one time-dependent value obtained in step (D) and said known permeability of said membrane for said gaseous constituent;

(F) comparing the target gas concentration so determined with a desired concentration of said target gas in said medium; and adding to, or removing from, said medium any amount of said target gas required to approach said desired concentration; and (G) repeating steps A–F for a desired number of repetitions so as to periodically fill said sensing space with a flushing gas and to intermittently permit permeation of said gaseous constituent.

15. The method as in claim 14, wherein said sensing space is in communication through a conduit with an ambient space so as to permit flow of said flushing gas and wherein diffusion of said flushing gas through said conduit is limited to a diffusion rate that does not exceed diffusion of said flushing gas from said sensing space through said membrane into said fluid medium.

16. The method as in claim 14, wherein an analog signal obtained in said measurement of step (D) is converted into a digital signal; and wherein said digital signal is used in step (E) for calculating said concentration by means of a digital computer.

17. The method as in claim 14, wherein said membrane comprises a film of an organic fluorocarbon polymer having a thickness in the range of from 1.5 to 150 micrometers.

18. The method as in claim 14, wherein said flushing gas is selected from substances that are substantially non-reactive when used under operating conditions of the method.

19. The method as in claim 14, wherein said permeation of said gaseous constituent through said membrane in step (C) is permitted during a period of from 20 to 60 seconds.

20. A method of controlling the concentration of a gas in a fluid medium comprising the steps of:

(A) pulsatingly measuring a specific diffusion parameter of said gas through a polymer membrane that is in contact with said fluid medium and is permeable for said gas but said membrane is substantially impermeable to any liquid component of said fluid medium;

(B) calculating said concentration from a previously determined general diffusion parameter of said gas through said polymer membrane;

(C) comparing said concentration obtained in step (B) with a predetermined concentration of said gas in said fluid medium; and (D) injecting an amount of said gas into said fluid medium so as to compensate a deficiency between said predetermined concentration and said concentration obtained in step (B).

21. An apparatus for controlling the concentration of a gas in a fluid medium comprising:

chamber means connected with a membrane in contact with said fluid medium that is permeable for said gas but is substantially impermeable for any liquid component of said medium, said chamber means defining a predetermined receiving volume and being connected with said membrane so as to permit diffusion of said gas across said membrane into said chamber means while preventing permeation of said liquid component of said fluid medium;

means in operative connection with said chamber means for determining the amount of gas that has accumulated in said receiving volume of said chamber means, during a measuring phase having a predetermined period of time, by diffusion of gas through said membrane into said chamber means;

means for removing, during a removal phase having a predetermined period of time, substantially all of said gas that has diffused into said chamber means;

means for cyclically repeating said removal phase and said measuring phase;

means for calculating an actual concentration of said gas in said fluid medium from a previously determined general diffusion parameter of said gas through said polymer membrane;

means for comparing said calculated concentration of said gas with a predetermined concentration of said gas in said fluid medium; and means to inject an amount of said gas into said medium to compensate a deficiency of said actual concentration relative to said predetermined concentration.

* * * * *